United States Patent
Nakamura

(10) Patent No.: US 11,992,179 B2
(45) Date of Patent: May 28, 2024

(54) POWER SUPPLY APPARATUS FOR ENDOSCOPE

(71) Applicant: OLYMPUS CORPORATION, Tokyo (JP)

(72) Inventor: Sho Nakamura, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 627 days.

(21) Appl. No.: 17/218,761

(22) Filed: Mar. 31, 2021

(65) Prior Publication Data

US 2021/0212551 A1 Jul. 15, 2021

Related U.S. Application Data

(63) Continuation of application No. PCT/JP2018/037005, filed on Oct. 3, 2018.

(51) Int. Cl.
*A61B 1/00* (2006.01)
*G02B 7/04* (2021.01)
(Continued)

(52) U.S. Cl.
CPC ...... *A61B 1/00025* (2013.01); *A61B 1/00006* (2013.01); *A61B 1/00188* (2013.01);
(Continued)

(58) Field of Classification Search
CPC ............ A61B 1/00006; A61B 1/00011; A61B 1/00018; A61B 1/00025; A61B 1/00036;
(Continued)

(56) References Cited

U.S. PATENT DOCUMENTS

| 2005/0148863 | A1* | 7/2005 | Okamura | A61B 5/418 600/422 |
| 2015/0374204 | A1* | 12/2015 | Tabuchi | A61B 1/00059 600/117 |
| 2016/0366328 | A1* | 12/2016 | Yamamoto | H04N 23/55 |

FOREIGN PATENT DOCUMENTS

| JP | 6013673 B1 | 10/2016 |
| JP | 6219004 B1 | 10/2017 |

(Continued)

OTHER PUBLICATIONS

International Search Report dated Dec. 18, 2018 received in PCT/JP2018/037005.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

A power supply apparatus for an endoscope includes a plurality of power supply circuits, a plurality of power changeover switches, and a power control circuit. The power control circuit performs an operation to determine, when one power changeover switch provided on one power supply line connecting one power supply circuit of the plurality of power supply circuits and one electronic part of the plurality of electronic parts in each order of the power-on sequence is set to off, whether an output voltage of the one power supply circuit is normal or not and an operation to start a supply of one drive voltage required to drive the one electronic part according to a judgement result that the output voltage of the one power supply circuit is normal.

5 Claims, 6 Drawing Sheets

(51) Int. Cl.
*G02B 23/24* (2006.01)
*A61B 1/045* (2006.01)
*H02J 4/00* (2006.01)

(52) U.S. Cl.
CPC .......... *G02B 7/04* (2013.01); *G02B 23/2407* (2013.01); *G02B 23/2476* (2013.01); *A61B 1/045* (2013.01); *H02J 4/00* (2013.01)

(58) Field of Classification Search
CPC ............ A61B 1/00057; A61B 1/00062; A61B 1/00188; A61B 1/05; A61B 1/045; A61B 1/00163; A61B 1/0019; A61B 1/00096; A61B 1/00097; A61B 1/00114; A61B 1/00117; A61B 1/00027; A61B 1/00029–00034; A61B 1/0008; A61B 1/00002; A61B 1/00004; A61B 1/00055; G02B 7/04; H02J 4/00; H02J 2310/23
USPC ................ 600/167–168, 173, 117–118, 103, 600/109–110, 160
See application file for complete search history.

(56) References Cited

FOREIGN PATENT DOCUMENTS

WO 2017/006575 A1 1/2017
WO 2017/203829 A1 11/2017

\* cited by examiner

POWER SUPPLY APPARATUS FOR ENDOSCOPE

CROSS REFERENCE TO RELATED APPLICATION

This application is a continuation application of PCT/JP2018/037005 filed on Oct. 3, 2018, the entire contents of which are incorporated herein by this reference.

BACKGROUND OF THE INVENTION

1. Field of the Invention

The present invention relates to a power supply apparatus for an endoscope.

2. Description of the Related Art

Endoscopes are generally provided with a plurality of electronic parts with different drive voltages. It is therefore necessary to supply power according to each of the plurality of electronic parts provided in each endoscope when using the endoscope. For example, Japanese Patent No. 6219004 discloses a configuration considered available for power supply to a plurality of electronic parts provided in each endoscope.

More specifically, Japanese Patent No. 6219004 discloses a camera control unit for an endoscope configured to supply power to each of the plurality of electronic parts such as an image pickup device provided in the endoscope. Japanese Patent No. 6219004 discloses a configuration with a switch provided on each power supply line connected to a plurality of electronic parts in an endoscope, in which control is performed to turn off the switch and then an output voltage to be supplied to each of the plurality of electronic parts is adjusted.

Here, among electronic parts provided in each endoscope, there may be electronic parts for which a power-on sequence is defined to prevent a drive voltage not applicable to rated operating conditions from being applied.

SUMMARY OF THE INVENTION

A power supply apparatus for an endoscope according to an aspect of the present invention is configured to supply power to an endoscope including a plurality of electronic parts for which a power-on sequence is defined, the power supply apparatus for an endoscope including a plurality of power supply circuits configured to generate a plurality of drive voltages required to drive each of the plurality of electronic parts, a plurality of power changeover switches provided in each of a plurality of power supply lines individually connecting the plurality of electronic parts and the plurality of power supply circuits, and a power control circuit configured to control the plurality of power supply circuits and the plurality of power changeover switches. The power control circuit performs a first operation and a second operation in each order of the power-on sequence. The first operation is to determine, when one power changeover switch provided on one power supply line connecting one power supply circuit of the plurality of power supply circuits and one electronic part of the plurality of electronic parts is set to off, whether an output voltage of the one power supply circuit is normal or not, and the second operation is to start a supply of one drive voltage required to drive the one electronic part according to a judgement result that the output voltage of the one power supply circuit is normal.

DETAILED DESCRIPTION OF THE PREFERRED EMBODIMENT

Hereinafter, an embodiment of the present invention will be described with reference to the accompanying drawings.

FIG. 1 to FIG. 7 relate to an embodiment of the present invention.

Figure 1:
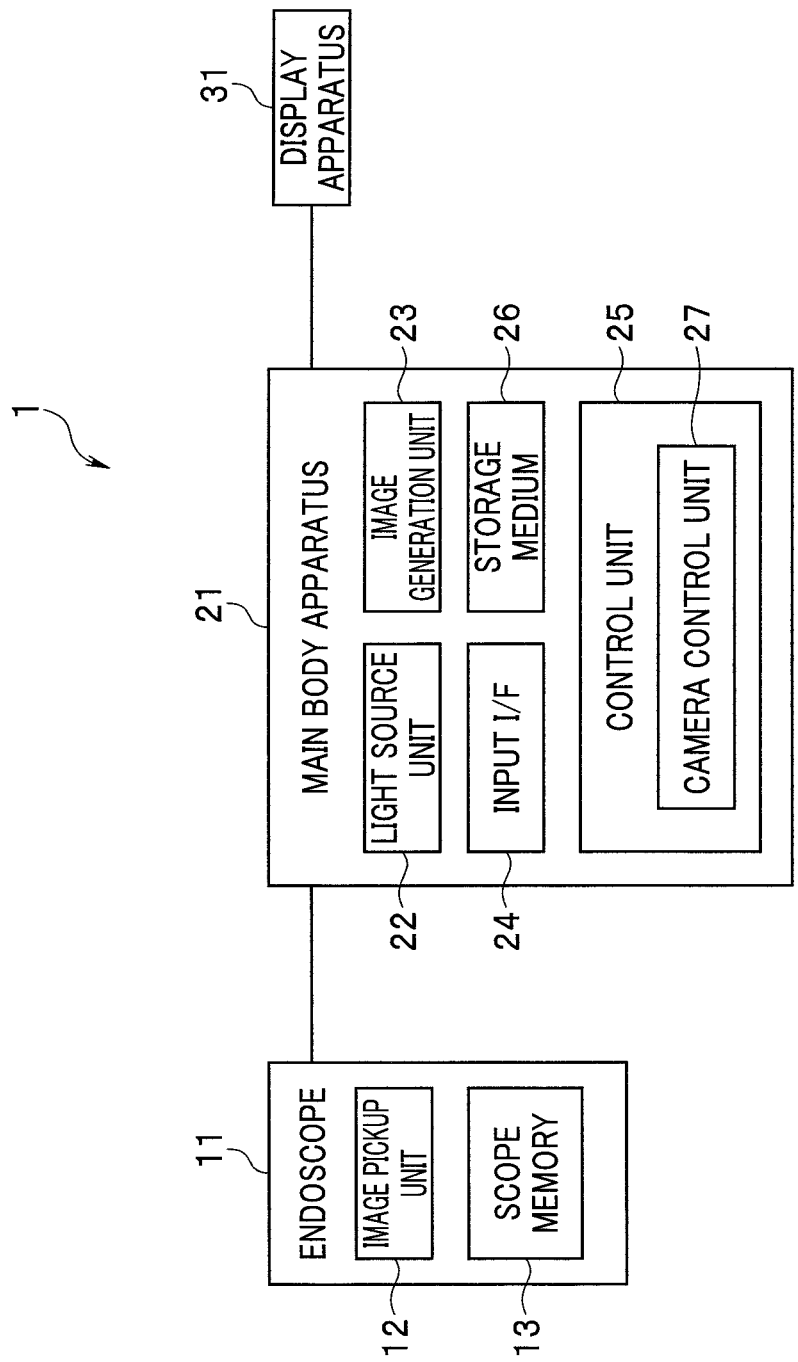
FIG. 1 is a diagram illustrating a configuration of main parts of an endoscope system according to an embodiment.

As illustrated, for example, in FIG. 1, an endoscope system 1 is constructed of an endoscope 11, a main body apparatus 21 and a display apparatus 31. FIG. 1 is a diagram illustrating a configuration of main parts of the endoscope system according to the embodiment.

The endoscope 11 is constructed, for example, of an elongated insertion portion (not shown), which is insertable into a subject or object, and an operation portion (not shown) provided at a proximal end portion of the insertion portion. The endoscope 11 is configured to be detachably connected to the main body apparatus 21 via a universal cable (not shown) extending from the operation portion. The endoscope 11 is internally provided with a light guide member (not shown) such as an optical fiber to guide illumination light supplied from the main body apparatus 21 and emit the illumination light from a distal end portion of the insertion portion. The endoscope 11 is constructed of an image pickup unit 12 and a scope memory 13.

Figure 2:
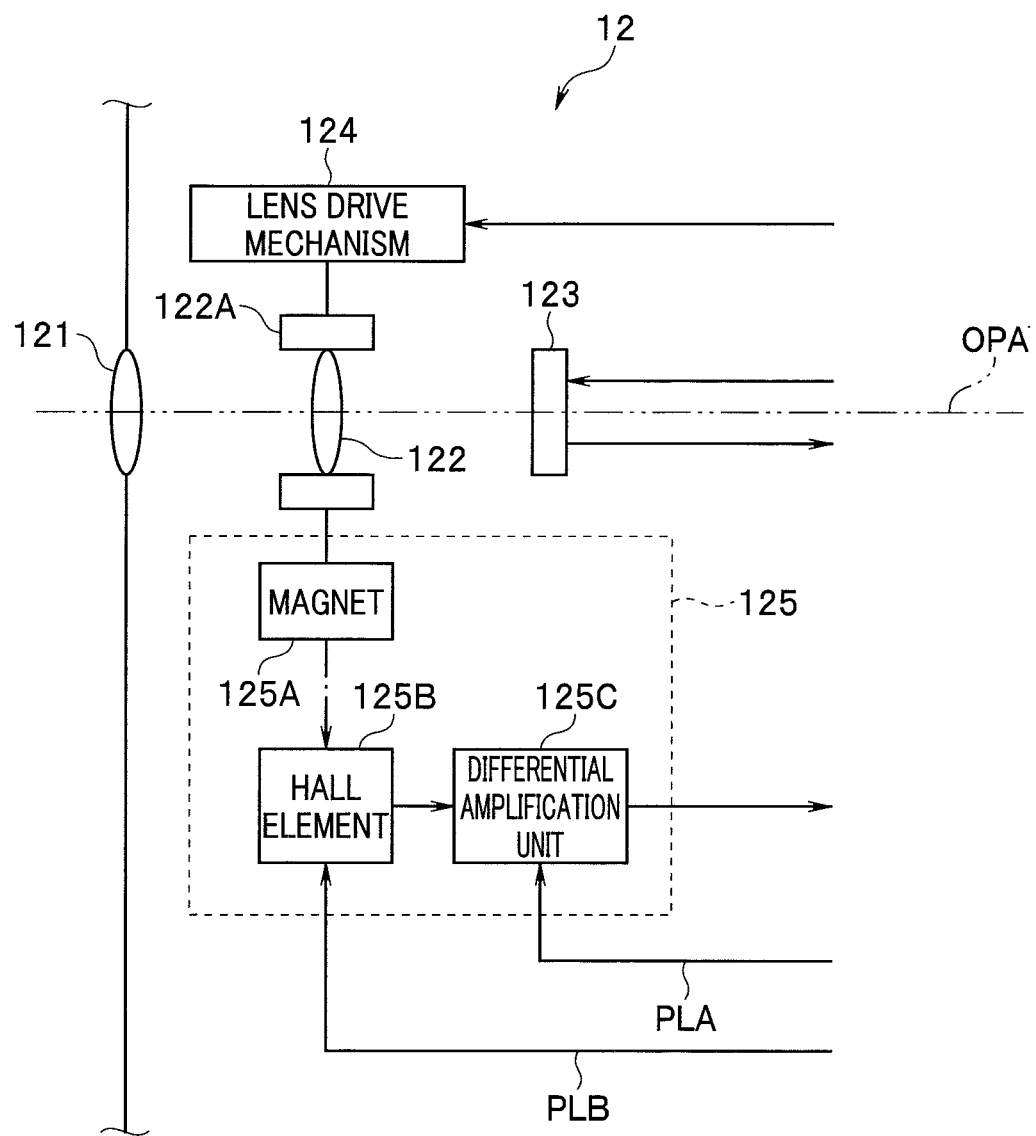
FIG. 2 is a diagram illustrating an example of a configuration of an image pickup unit provided in the endoscope according to the embodiment.

The image pickup unit 12 is provided at the distal end portion of the insertion portion of the endoscope 11. As illustrated in FIG. 2, the image pickup unit 12 is constructed, for example, of an objective lens 121, an image forming lens 122, an image pickup device 123, a lens drive mechanism 124 and a lens position detection mechanism 125. FIG. 2 is a diagram illustrating an example of a configuration of the image pickup unit provided in the endoscope according to the embodiment.

The objective lens 121 is attached to an observation window (not shown) provided at the distal end portion of the insertion portion of the endoscope 11. The objective lens 121 is configured, for example, to have an optical axis OPA parallel to a longitudinal axis direction of the insertion portion of the endoscope 11. The objective lens 121 is also configured to obtain an optical image corresponding to return light from a subject or object illuminated with illumination light emitted through the distal end portion of the insertion portion of the endoscope 11.

The image forming lens 122 is held by a lens frame 122A. The image forming lens 122 is configured to form the optical image obtained by the objective lens 121. The image forming lens 122 is configured to be able to move along the direction of the optical axis OPA according to operation of the lens drive mechanism 124 attached to the lens frame 122A.

The image pickup device 123 is constructed of an image sensor such as a CCD or a CMOS. The image pickup device 123 is constructed of a plurality of pixels to pick up an image by photoelectrically converting an optical image formed by the image forming lens 122 and a color filter provided on an image pickup surface on which the plurality of pixels are two-dimensionally arranged. Note that the aforementioned color filter is formed of R (red color), G (green color) and B (blue color) micro filters arranged in a Bayer array at positions corresponding to respective pixels of the image pickup device 123. The image pickup device 123 is configured to be driven according to image pickup device drive signals supplied from the main body apparatus 21. The image pickup device 123 is configured to generate an image pickup signal by picking up an optical image from an image formed by the image forming lens 122 and output the generated image pickup signal to the main body apparatus 21.

The lens drive mechanism 124 is constructed, for example, of a voice coil motor, a piezoelectric element or a shape-memory alloy. The lens drive mechanism 124 is configured to be able to perform operation to move the image forming lens 122 (lens frame 122A) within a predetermined movable range between a light emission surface of the objective lens 121 and an image pickup surface of the image pickup device 123 according to a lens drive signal supplied from the main body apparatus 21.

The lens position detection mechanism 125 is configured to detect a current position of the image forming lens 122 (lens frame 122A) that moves according to the operation of the lens drive mechanism 124, generate a lens position detection signal indicating the detected current position of the image forming lens 122 (lens frame 122A) and output the generated lens position detection signal to the main body apparatus 21. The lens position detection mechanism 125 is constructed of a magnet 125A attached to the lens frame 122A, a Hall element 125B and a differential amplification unit 125C as illustrated, for example, in FIG. 2.

The magnet 125A is attached, for example, to an outer circumferential portion of the lens frame 122A and configured to be able to move as the image forming lens 122 moves. The magnet 125A is configured to generate a magnetic field in the vicinity of a position where the image forming lens 122 (lens frame 122A) is currently located.

The Hall element 125B is configured to detect the magnetic field emitted from the magnet 125A, generate a magnetic field detection signal corresponding to strength of the detected magnetic field and output the generated magnetic field detection signal to the differential amplification unit 125C. The Hall element 125B is connected to a camera control unit 27 (which will be described later) of the main body apparatus 21 via a power supply line PLB and configured to operate using a drive voltage supplied via the power supply line PLB.

The differential amplification unit 125C includes an operational amplifier or the like. The differential amplification unit 125C is configured to amplify the magnetic field detection signal outputted from the Hall element 125B and output the amplified magnetic field detection signal to the main body apparatus 21 as a lens position detection signal. The differential amplification unit 125C is connected to the camera control unit 27 of the main body apparatus 21 via a power supply line PLA and configured to operate using a drive voltage supplied via the power supply line PLA.

The scope memory 13 stores endoscope information including information specific to the endoscope 11. The endoscope information stored in the scope memory 13 is read by a control unit 25 and a power control unit 277 (both will be described later) of the main body apparatus 21 when the endoscope 11 and the main body apparatus 21 are electrically connected together and power of the main body apparatus 21 is turned on.

The main body apparatus 21 is configured to be detachably connected to the endoscope 11 and the display apparatus 31 respectively. As illustrated, for example, in FIG. 1, the main body apparatus 21 is constructed of a light source unit 22, an image generation unit 23, an input I/F (interface) 24, the control unit 25 and a storage medium 26.

The light source unit 22 is constructed of one or more light-emitting devices such as an LED. More specifically, the light source unit 22 is constructed of a blue LED that generates blue light (hereinafter also referred to as "B light"), a green LED that generates green light (hereinafter also referred to as "G light") and a red LED that generates red light (hereinafter also referred to as "R light"). The light source unit 22 is configured to be able to generate illumination light corresponding to control of the control unit 25 and supply the illumination light to the endoscope 11.

The image generation unit 23 is constructed, for example, of an image generation circuit. The image generation unit 23 is configured to generate an endoscopic image based on an image pickup signal outputted from the endoscope 11 and output the generated endoscopic image to the display apparatus 31.

The input I/F 24 is provided with one or more switches that can give instructions to the control unit 25 according to a user's input operation.

The control unit 25 is configured to perform control relating to operation of each unit of the endoscope 11 and the main body apparatus 21 based on instructions given by the input I/F 24 and/or endoscope information read from the scope memory 13. The control unit 25 includes the camera control unit 27 that performs operation relating to control of the image pickup unit 12.

The camera control unit 27 is configured to generate an image pickup device drive signal to drive the image pickup device 123 and output the image pickup device drive signal to the endoscope 11.

Figure 3:
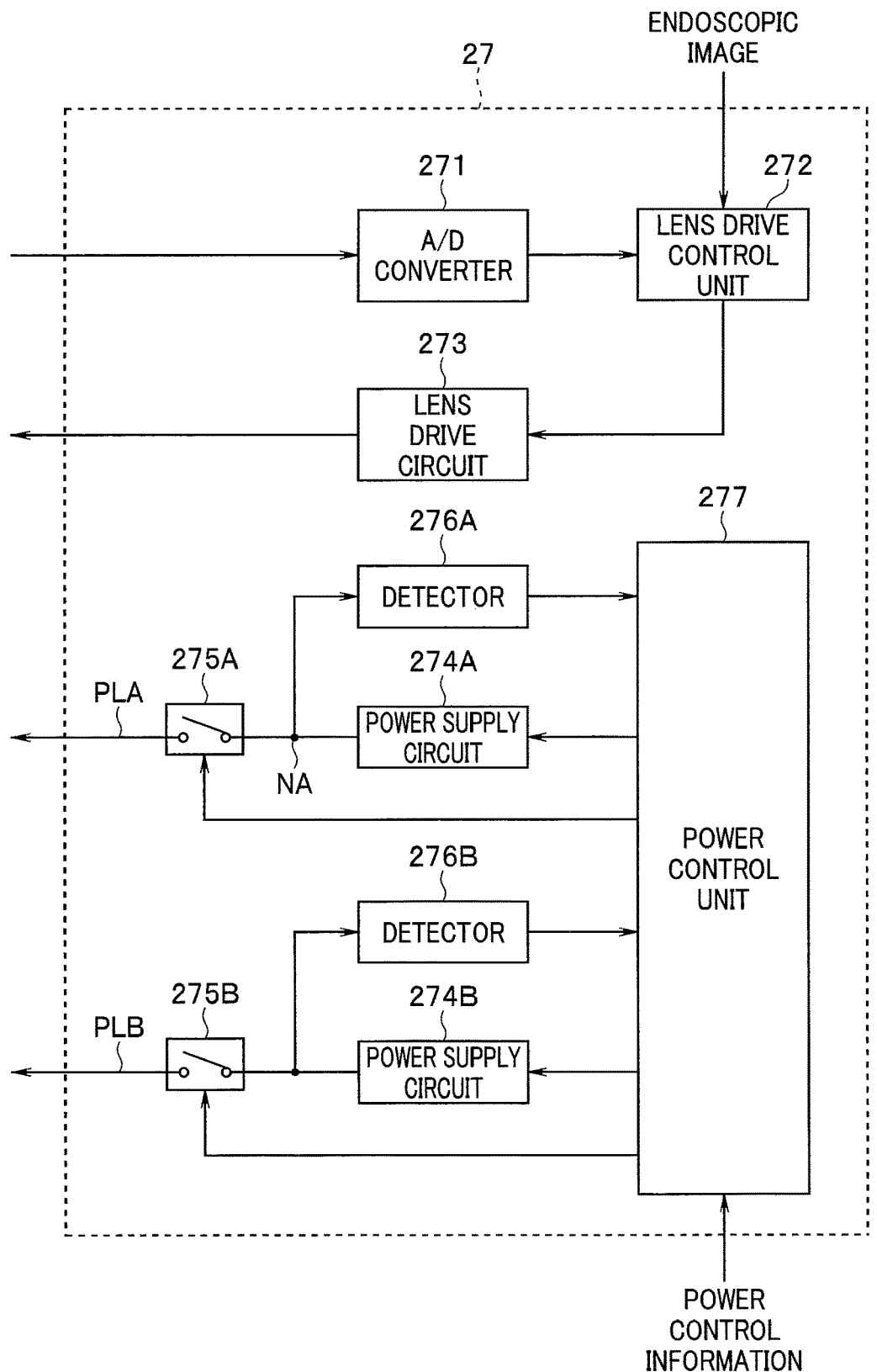
FIG. 3 is a diagram illustrating an example of a configuration of a camera control unit according to the embodiment.

The camera control unit 27 is configured to include a function as the power supply apparatus for an endoscope that supplies power to the endoscope including a plurality of electronic parts for which a power-on sequence is defined. As illustrated in FIG. 3, the camera control unit 27 is configured to include an A/D converter 271, a lens drive control unit 272, a lens drive circuit 273, power supply circuits 274A and 274B, power changeover switches 275A and 275B, detectors 276A and 276B and the power control unit 277. FIG. 3 is a diagram illustrating an example of a configuration of the camera control unit according to the embodiment.

The A/D converter 271 is configured to convert the lens position detection signal outputted from the endoscope 11 to a digital signal and output the digital signal to the lens drive control unit 272.

The lens drive control unit 272 is constructed, for example, of a lens drive control circuit. The lens drive control unit 272 is configured to control the lens drive circuit 273 so as to dispose the image forming lens 122 at a position where the endoscopic image is in focus based on the endoscopic image generated by the image generation unit 23 and the digital signal outputted from the A/D converter 271.

The lens drive circuit 273 is configured to generate a lens drive signal to drive the lens drive mechanism 124 according to the control of the lens drive control unit 272 and output the lens drive signal to the endoscope 11.

The power supply circuit 274A is connected to the differential amplification unit 125C of the endoscope 11 via the power supply line PLA. The power supply circuit 274A is configured to generate and output an output voltage according to the control of the power control unit 277 using a supply voltage supplied from an external power supply (not shown) such as a commercial power supply. The power supply circuit 274A is configured to be able to generate a drive voltage required to drive the differential amplification unit 125C using a supply voltage supplied from an external power supply such as a commercial power supply.

The power changeover switch 275A is provided on the power supply line PLA connecting the power supply circuit 274A and the differential amplification unit 125C and is configured to be set (switched) to either on or off according to the control of the power control unit 277.

The detector 276A is configured to detect a voltage value of a voltage applied to a section of the power supply line PLA between the power supply circuit 274A and the power changeover switch 275A and output the detected voltage value to the power control unit 277. The detector 276A is also configured to detect a current value of a current applied to the section of the power supply line PLA between the power supply circuit 274A and the power changeover switch 275A and output the detected current value to the power control unit 277.

The power supply circuit 274B is connected to the Hall element 125B of the endoscope 11 via the power supply line PLB. The power supply circuit 274B is configured to generate and output an output voltage according to the control of the power control unit 277 using a supply voltage supplied from an external power supply such as a commercial power supply. The power supply circuit 274B is also configured to be able to generate a drive voltage required to drive the Hall element 125B using a supply voltage supplied from an external power supply such as a commercial power supply.

The power changeover switch 275B is provided on the power supply line PLB connecting the power supply circuit 274B and the Hall element 125B and is configured to be set (switched) to either on or off according to the control of the power control unit 277.

The detector 276B is configured to detect a voltage value of a voltage applied to a section of the power supply line PLB between the power supply circuit 274B and the power changeover switch 275B and output the detected voltage value to the power control unit 277. The detector 276B is configured to detect a current value of a current applied to the section of the power supply line PLB between the power supply circuit 274B and the power changeover switch 275B and output the detected current value to the power control unit 277.

The power control unit 277 is constructed, for example, of a power control circuit. The power control unit 277 is configured to control output voltages outputted from the power supply circuits 274A and 274B. The power control unit 277 is configured to perform control to set the power changeover switch 275A to either on or off. The power control unit 277 is configured to perform control to set the power changeover switch 275B to either on or off. In other words, the power control unit 277 is configured to control the power supply circuits 274A and 274B, and the power changeover switches 275A and 275B. The power control unit 277 is configured to read power control information (which will be described later) stored in the storage medium 26 when power of the main body apparatus 21 is turned on. The power control unit 277 is also configured to operate based on the power control information read from the storage medium 26. Note that specific examples of the operation performed by the power control unit 277 based on the power control information read from the storage medium 26 will be described later.

The storage medium 26 stores information such as power control information used by the power control unit 277. The aforementioned power control information includes, for example, information indicating a control sequence in the control on the power supply circuits 274A and 274B, information indicating a voltage value range of a drive voltage required to drive the Hall element 125B and information indicating a voltage value range of a drive voltage required to drive the differential amplification unit 125C.

The display apparatus 31 is constructed, for example, of a monitor. The display apparatus 31 is configured to be able to display an endoscopic image outputted from the main body apparatus 21.

Figure 4:
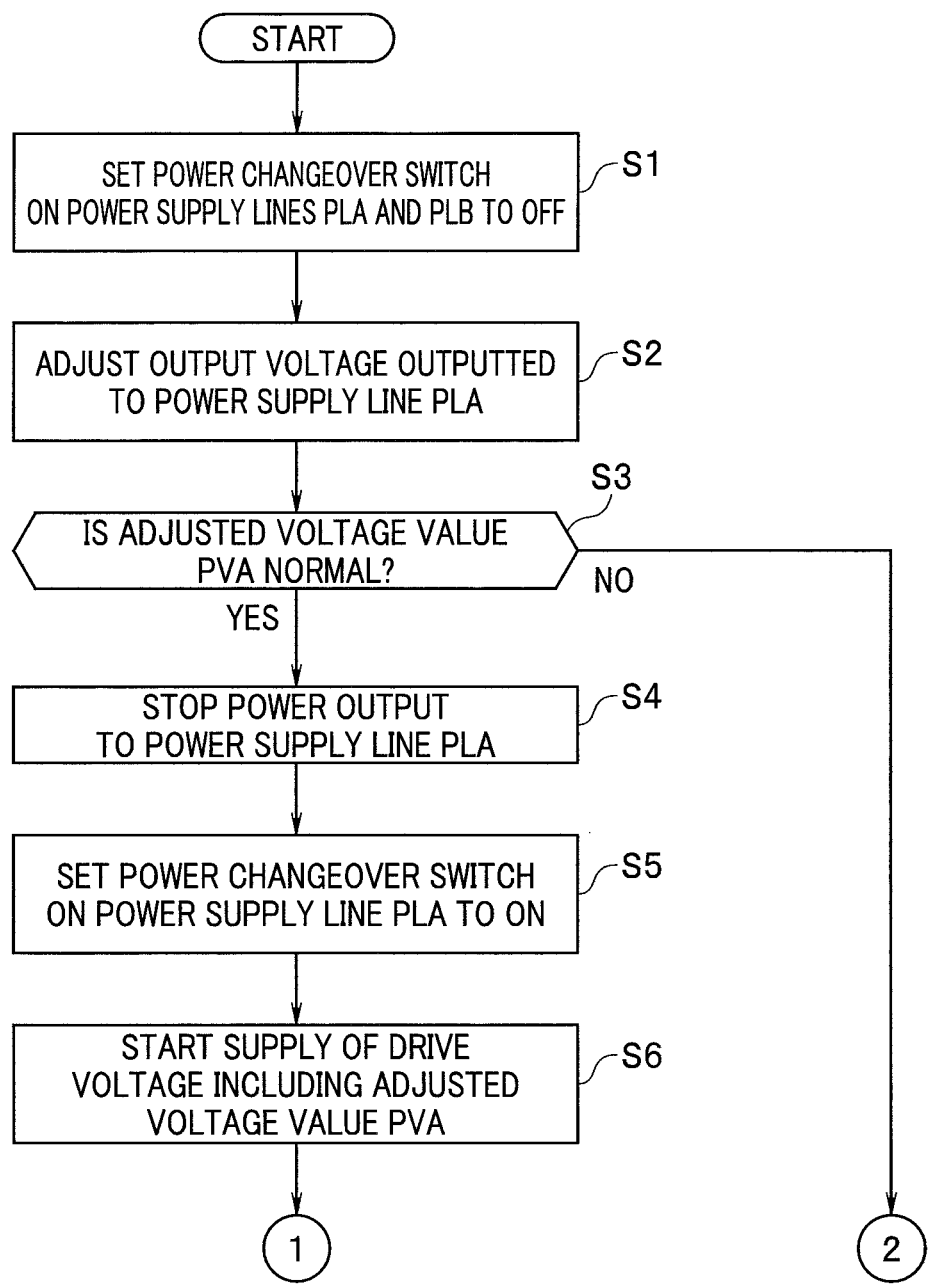
FIG. 4 is a flowchart illustrating part of a specific example of processing or the like executed by the camera control unit according to the embodiment.
Figure 5:
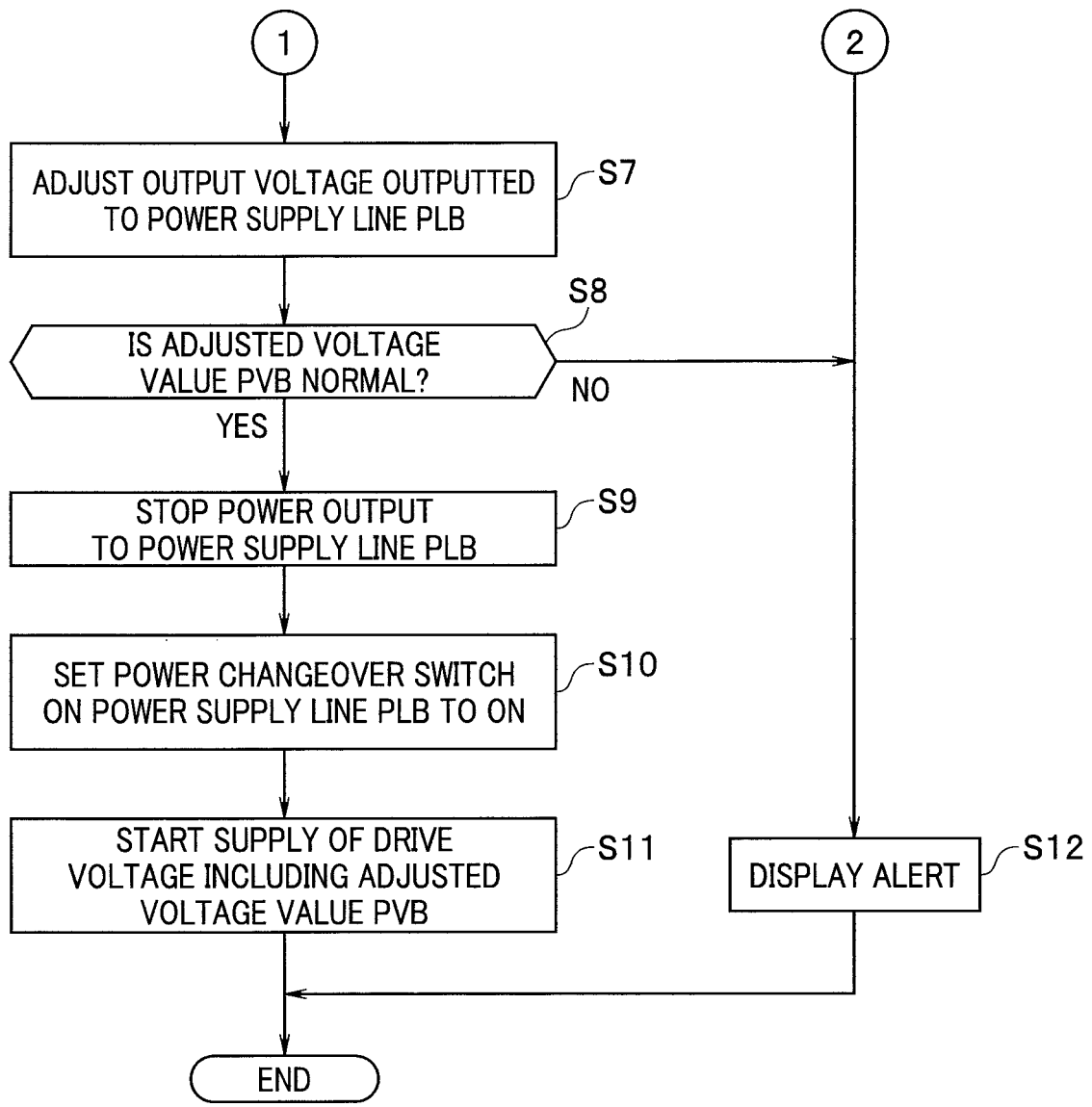
FIG. 5 is a flowchart illustrating a continuation of the processing in FIG. 4.

Next, operation of the present embodiment will be described with reference to FIG. 4 and FIG. 5. Note that the description hereinafter assumes that the power-on sequence of the lens position detection mechanism 125 is defined such that a drive voltage is supplied to the Hall element 125B after a drive voltage is supplied to the differential amplification unit 125C. Furthermore, the description hereinafter assumes that the control sequence included in the power control information stored in the storage medium 26 is created according to the power-on sequence of the lens position detection mechanism 125. FIG. 4 is a flowchart illustrating part of a specific example of processing or the like executed by the camera control unit included in the endoscope system according to the embodiment. FIG. 5 is a flowchart illustrating a continuation of the processing in FIG. 4.

When the power of the main body apparatus 21 is turned on, the power control unit 277 performs control to set the power changeover switch 275A on the power supply line PLA and the power changeover switch 275B on the power supply line PLB to off (step S1 in FIG. 4). When the power of the main body apparatus 21 is turned on, the power control unit 277 reads power control information stored in the storage medium 26. After performing the operation in step S1 in FIG. 4, the power control unit 277 performs operation based on the control sequence included in the power control information read from the storage medium 26. In other words, the power control unit 277 performs control to set the power changeover switch 275A on the power supply line PLA and the power changeover switch 275B on the power supply line PLB to off before performing operation relating to the power-on sequence of (the Hall element 125B and the differential amplification unit 125C included in) the lens position detection mechanism 125.

Based on the power control information read from the storage medium 26, the power control unit 277 identifies that the voltage value range of a drive voltage required to drive the differential amplification unit 125C is equal to or more than a voltage value DVA and equal to or less than a voltage value DVB. Note that the voltage values DVA and DVB are supposed to be set to voltage values less than a supply voltage value supplied from an external power supply such as a commercial power supply to the power supply circuit 274A.

In order for the voltage value outputted from the detector 276A to fall within a range of the voltage value DVA or more and the voltage value DVB or less, the power control unit 277 performs operation for adjusting the output voltage outputted from the power supply circuit 274A to the power supply line PLA (step S2 in FIG. 4).

After performing the operation in step S2 in FIG. 4 for a certain time period, the power control unit 277 determines whether the adjusted voltage value PVA outputted from the detector 276A is normal or not (step S3 in FIG. 4).

When the power control unit 277 detects that the adjusted voltage value PVA belongs to the range of the voltage value DVA or more and the voltage value DVB or less, the power control unit 277 acquires a judgement result that the adjusted voltage value PVA is normal (S3: YES) and then performs operation in step S4 in FIG. 4, which will be described later. When the power control unit 277 detects that the adjusted voltage value PVA deviates from the range of the voltage value DVA or more and the voltage value DVB or less, the power control unit 277 acquires a judgement result that the adjusted voltage value PVA is abnormal (S3: NO) and then performs operation in step S12 in FIG. 5, which will be described later.

The power control unit 277 performs operation for temporarily stopping power output from the power supply circuit 274A to the power supply line PLA (step S4 in FIG. 4). After performing the operation in step S4 in FIG. 4, the power control unit 277 sets the power changeover switch 275A on the power supply line PLA to on (step S5 in FIG. 4). Based on the voltage value outputted from the detector 276A, the power control unit 277 controls the power supply circuit 274A to start a supply of a drive voltage having the adjusted voltage value PVA obtained in step S3 in FIG. 4 (step S6 in FIG. 4).

In other words, in a first step of the power-on sequence of (the Hall element 125B and the differential amplification unit 125C included in) the lens position detection mechanism 125, the power control unit 277 performs operation to determine whether the output voltage of the power supply circuit 274A is normal or not and performs operation to start a supply of a drive voltage having the adjusted voltage value PVA according to the judgement result that the output voltage of the power supply circuit 274A is normal with the power changeover switch 275A provided on the power supply line PLA connecting the power supply circuit 274A and the differential amplification unit 125C set to off. When the power control unit 277 obtains a judgement result that the voltage value outputted from the detector 276A is normal, the power control unit 277 performs control to temporarily stop power output from the power supply circuit 274A to the power supply line PLA, performs control to switch the power changeover switch 275A from off to on, and then performs control to start a supply of the drive voltage having the adjusted voltage value PVA from the power supply circuit 274A.

According to the aforementioned operation, with the power changeover switch 275A on the power supply line PLA set to off, the output voltage to be outputted from the power supply circuit 274A to the power supply line PLA is adjusted and it is determined whether the voltage value outputted from the detector 276A is normal or not.

Based on the power control information read from the storage medium 26, the power control unit 277 identifies that the voltage value range of a drive voltage required to drive the Hall element 125B is equal to or more than a voltage value DVM and equal to or less than a voltage value DVN. Note that the voltage values DVM and DVN are supposed to be set to voltage values less than the supply voltages supplied from an external power supply such as a commercial power supply to the power supply circuit 274B.

In order for the voltage value outputted from the detector 276B to fall within a range of the voltage value DVM or more and the voltage value DVN or less, the power control unit 277 performs operation for adjusting the output voltage outputted from the power supply circuit 274B to the power supply line PLB (step S7 in FIG. 5).

After performing the operation in step S7 in FIG. 5 for a certain time period, the power control unit 277 determines whether the adjusted voltage value PVB outputted from the detector 276B is normal or not (step S8 in FIG. 5).

When the power control unit 277 detects that the adjusted voltage value PVB belongs to the range of the voltage value DVM or more and the voltage value DVN or less, the power control unit 277 acquires a judgement result that the adjusted voltage value PVB is normal (S8: YES) and then performs the operation in step S9 in FIG. 5, which will be described later. When the power control unit 277 detects that the adjusted voltage value PVB deviates from the range of the voltage value DVM or more and the voltage value DVN or less, the power control unit 277 acquires a judgement result that the adjusted voltage value PVB is abnormal (S8: NO) and then performs the operation in step S12 in FIG. 5, which will be described later.

The power control unit 277 performs operation for temporarily stopping power output from the power supply circuit 274B to the power supply line PLB (step S9 in FIG. 5). After performing the operation in step S9 in FIG. 5, the power control unit 277 sets the power changeover switch 275B on the power supply line PLB to on (step S10 in FIG. 5). Based on the voltage value outputted from the detector 276B, the power control unit 277 controls the power supply circuit 274B to start a supply of a drive voltage having the adjusted voltage value PVB obtained in step S8 in FIG. 5 (step S11 in FIG. 5), and then ends a series of operations based on the control sequence included in the power control information read from the storage medium 26.

In other words, in a second step of the power-on sequence of (the Hall element 125B and the differential amplification unit 125C included in) the lens position detection mechanism 125, the power control unit 277 performs operation to determine whether the output voltage of the power supply circuit 274B is normal or not and performs operation to start a supply of a drive voltage having the adjusted voltage value PVB according to the judgement result that the output voltage of the power supply circuit 274B is normal with the power changeover switch 275B provided on the power supply line PLB connecting the power supply circuit 274B and the Hall element 125B set to off. When the power control unit 277 obtains a judgement result that the voltage value outputted from the detector 276B is normal, the power control unit 277 performs control to temporarily stop power output from the power supply circuit 274B to the power supply line PLB, performs control to switch the power changeover switch 275B from off to on, and then performs control to start a supply of the drive voltage having the adjusted voltage value PVB from the power supply circuit 274B.

According to the aforementioned operation, when a supply of the drive voltage from the power supply circuit 274A to the differential amplification unit 125C is started and the power changeover switch 275B on the power supply line PLB is set to off, the output voltage outputted from the power supply circuit 274B to the power supply line PLB is adjusted, and it is determined whether the voltage value outputted from the detector 276B is normal or not.

When the power control unit 277 acquires a judgement result that the adjusted voltage value PVA is abnormal, the power control unit 277 performs operation to cause the display apparatus 31 to display an alert including a character string or the like indicating that a defect has occurred, for example, in the power supply circuit 274A or in periphery of the power supply circuit 274A (step S12 in FIG. 5), and then ends a series of operations based on the control sequence included in the power control information read from the storage medium 26. When the power control unit 277 acquires a judgement result that the adjusted voltage value PVB is abnormal, the power control unit 277 performs operation to cause the display apparatus 31 to display an alert including a character string or the like indicating that a defect has occurred in the power supply circuit 274B or in periphery of the power supply circuit 274B (step S12 in FIG. 5), and then ends a series of operations based on the control sequence included in the power control information read from the storage medium 26.

As described so far, according to the present embodiment, when it is confirmed that the output voltage outputted from the power supply circuit 274A to the power supply line PLA is normal and a supply of a drive voltage from the power supply circuit 274A to the differential amplification unit 125C is started, operation for confirming whether the output voltage outputted from the power supply circuit 274B to the power supply line PLB is normal or not is performed. Therefore, according to the present embodiment, even when a situation occurs in which the power changeover switch 275B on the power supply line PLB is unintentionally kept on (without following the control of the power control unit 277), it is possible to prevent defects from occurring due to a supply of the drive voltage to the Hall element 125B started before the differential amplification unit 125C. Therefore, according to the present embodiment, it is possible to prevent defects from occurring due to power to the plurality of electronic parts provided in the endoscope being turned on in an originally unintentional sequence.

As described above, according to the present embodiment, when a judgement result that the adjusted voltage value PVA is normal is acquired, a supply of the drive voltage is restarted after temporarily stopping the power output from the power supply circuit 274A to the power supply line PLA. Therefore, according to the present embodiment, it is possible to prevent peak noise due to a changeover of the power changeover switch 275A from on to off when the power output from the power supply circuit 274A is in progress.

As described above, according to the present embodiment, when a judgement result that the adjusted voltage value PVB is normal is acquired, the power output from the power supply circuit 274B to the power supply line PLB is temporarily stopped and the supply of the drive voltage is then restarted. Therefore, according to the present embodiment, it is possible to prevent peak noise due to a changeover of the power changeover switch 275B from off to on when the power output from the power supply circuit 274B is in progress.

Note that according to the present embodiment, information indicating a voltage value range of the drive voltage required to drive the Hall element 125B and information indicating a voltage value range of the drive voltage required to drive the differential amplification unit 125C may be included in the endoscope information stored in the scope memory 13. In other words, the power control unit 277 of the present embodiment may be configured to identify a range of a voltage value used to determine whether the output voltage of the power supply circuit 274A is normal or not and a range of a voltage value used to determine whether the output voltage of the power supply circuit 274B is normal or not based on the endoscope information read from the scope memory 13 provided in the endoscope 11.

Figure 6:
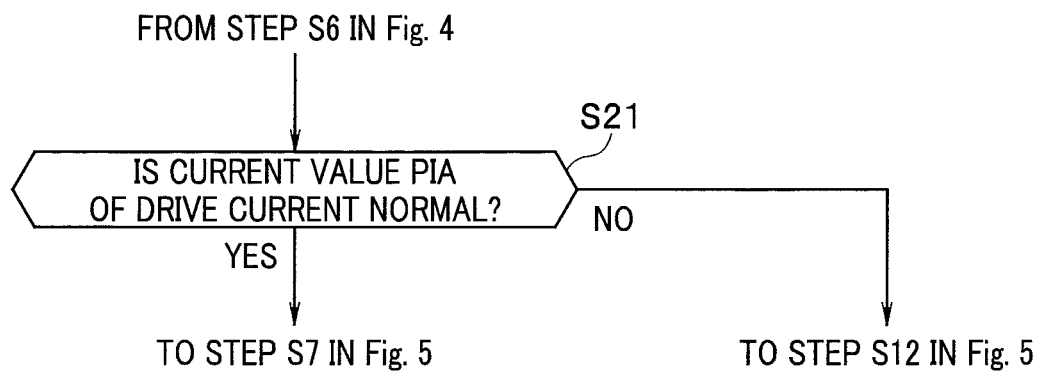
FIG. 6 is a diagram for describing processing executed by a camera control unit according to a modification of the embodiment.
Figure 7:
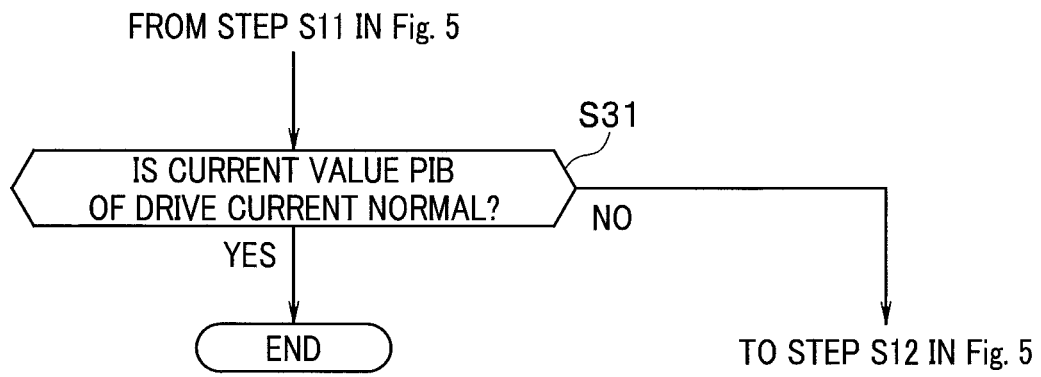
FIG. 7 is a diagram for describing processing executed by the camera control unit according to the modification of the embodiment.

According to the present embodiment, for example, when information indicating the current value range of the drive current required to drive the Hall element 125B and information indicating the current value range of the drive current required to drive the differential amplification unit 125C are stored in the scope memory 13, operation according to a modification as illustrated in FIG. 6 and FIG. 7 may further be performed. Specific examples of such an operation according to the modifications will be described below. Note that specific description relating to parts to which operations already described are applicable will be omitted as appropriate. FIG. 6 and FIG. 7 are diagrams for describing processing executed by a camera control unit according to a modification of the embodiment.

Based on the endoscope information read from the scope memory 13, the power control unit 277 identifies that the current value range of the drive current required to drive the differential amplification unit 125C is a current value DIA or more and a current value DIB or less. In other words, the power control unit 277 identifies the current value range to be used for determination in step S21 in FIG. 6, which will be described later, based on the endoscope information read from the scope memory 13. Note that the current values DIA and DIB may be set as values according to operating conditions such as a rated current of the differential amplification unit 125C.

After performing the operation in step S6 in FIG. 4, the power control unit 277 determines whether the current value PIA of the drive current outputted from the detector 276A is normal or not (step S21 in FIG. 6). In other words, after performing the operation to start a supply of a drive voltage having the adjusted voltage value PVA, the power control unit 277 performs operation to determine whether the drive current flowing into the power supply line PLA is normal or not.

When the power control unit 277 detects that the current value PIA of the drive current belongs to a range of a current value DIA or more and a current value DIB or less, the power control unit 277 acquires a judgement result that the current value PIA of the drive current is normal (S21: YES) and then performs the aforementioned operation in step S7 in FIG. 5. On the other hand, when the power control unit 277 detects that the current value PIA of the drive current deviates from a range of a current value DIA or more and a current value DIB or less, the power control unit 277 acquires a judgement result that the current value PIA of the drive current is abnormal (S21: NO) and then performs the aforementioned operation in step S12 in FIG. 5.

Based on the endoscope information read from the scope memory 13, the power control unit 277 identifies, for example, that the current value range of a drive current required to drive the Hall element 125B is a current value DIM or more and a current value DIN or less. In other words, the power control unit 277 identifies a current value range to be used for determination in step S31 in FIG. 7, which will be described later, based on the endoscope information read from the scope memory 13. Note that the current values DIM and DIN may be set as values according to operating conditions such as a rated current of the Hall element 125B.

After performing the operation in step S11 in FIG. 5, the power control unit 277 determines whether the current value PIB of the drive current outputted from the detector 276B is normal or not (step S31 in FIG. 7). In other words, after performing the operation to start a supply of a drive voltage having the adjusted voltage value PVB, the power control unit 277 performs operation to determine whether the drive current flowing into the power supply line PLB is normal or not.

When the power control unit 277 detects that the current value PIB of the drive current belongs to a range of the current value DIM or more and the current value DIN or less, the power control unit 277 acquires a judgement result that the current value PIB of the drive current is normal (S31: YES) and then ends a series of operations based on the control sequence included in the power control information read from the storage medium 26. On the other hand, when the power control unit 277 detects that the current value PIB of the drive current deviates from a range of the current value DIM or more and the current value DIN or less, the power control unit 277 acquires a judgement result that the current value PIB of the drive current is abnormal (S31: NO) and then performs the aforementioned operation in step S12 in FIG. 5.

As described above, according to the present modification, before performing the operation to confirm whether the output voltage outputted from the power supply circuit 274B to the power supply line PLB is normal or not, it is determined whether the current value PIA of the drive current flowing into the power supply line PLA is normal or not. Therefore, according to the present modification, even when a situation occurs in which the power changeover switch 275A on the power supply line PLA is unintentionally kept off (without following the control of the power control unit 277), it is possible to prevent defects from occurring due to a supply of the drive voltage to the Hall element 125B started before the differential amplification unit 125C.

Note that the aforementioned embodiment and modification are not limited to those applied to supply power for two electronic parts of the Hall element 125B and the differential amplification unit 125C, but may be modified as appropriate so as to be applicable to supplying power to three or more electronic parts for which a power-on sequence is defined. In other words, the aforementioned embodiment and modification are applicable to supplying power to a plurality of electronic parts for which a power-on sequence is defined.

What is claimed is:

1. A power supply apparatus for supplying power to an endoscope comprising a plurality of electronic parts for which a power-on sequence is defined, the power supply apparatus comprising:
   a plurality of power supply circuits configured to generate a plurality of drive voltages required to drive each of the plurality of electronic parts;
   a plurality of power changeover switches provided in each of a plurality of power supply lines individually connecting the plurality of electronic parts and the plurality of power supply circuits; and
   a power control circuit configured to control the plurality of power supply circuits and the plurality of power changeover switches,
   wherein the power control circuit is configured to perform a first operation and a second operation for each of the plurality of electronic parts in the power-on sequence defined,
   wherein in the first operation, the power control circuit is configured to determine, when one power changeover switch provided on one power supply line connecting one power supply circuit of the plurality of power supply circuits and one electronic part of the plurality of electronic parts is set to off, whether an output voltage of the one power supply circuit is normal or not, and
   wherein in the second operation, the power control circuit is configured to:
   in response to determining that the output voltage of the one power supply circuit is normal, and with the one power changeover switch being set to off, control to temporarily stop power output from the one power supply circuit to the one power supply line;
   control, with power output from the one power supply circuit being temporarily stopped, to switch the one power changeover switch from off to on; and
   perform, when the one power changeover switch is controlled to switch from off to on, control to start a supply of one drive voltage required to drive the one electronic part from the power supply circuit.

2. The power supply apparatus according to claim 1, wherein the power control circuit is configured to, after performing the second operation, perform a third operation to determine whether a drive current flowing into the one power supply line is normal or not.

3. The power supply apparatus according to claim 2, wherein the power control circuit is configured to:
   identify a range of a current value used to determine whether the drive current is normal or not based on endoscope information read from a memory provided in the endoscope; and
   in the third operation, determine whether the drive current is normal or not based on the range of the current value identified.

4. The power supply apparatus according to claim 1, wherein the power control circuit is configured to:
   identify a range of a voltage value used to determine whether the output voltage of the one power supply circuit is normal or not based on endoscope information read from a memory provided in the endoscope; and
   in the first operation, determine whether the output voltage of the one power supply circuit is normal or not based on the range of the voltage value identified.

5. The power supply apparatus according to claim 1, wherein the endoscope comprises a lens, a lens drive actuator configured to move the lens along a direction of an optical axis and a lens position detection sensor configured to detect a current position of the lens and output a signal indicating the current position of the lens, and
   wherein the plurality of electronic parts are provided in the lens position detection sensor.

* * * * *